United States Patent
Fleenor et al.

(10) Patent No.: US 7,813,800 B2
(45) Date of Patent: Oct. 12, 2010

(54) INDICATING THE STATUS OF AN ENERGY STORAGE DEVICE OF A MEDICAL DEVICE

(75) Inventors: Susan H. Fleenor, Kenmore, WA (US); John C. Daynes, Redmond, WA (US)

(73) Assignee: Physio-Control, Inc., Redmond, WA (US)

(*) Notice: Subject to any disclaimer, the term of this patent is extended or adjusted under 35 U.S.C. 154(b) by 39 days.

(21) Appl. No.: 10/964,509

(22) Filed: Oct. 13, 2004

(65) Prior Publication Data

US 2006/0079938 A1    Apr. 13, 2006

(51) Int. Cl.
    *A61N 1/00*    (2006.01)
(52) U.S. Cl. ........................................ 607/29
(58) Field of Classification Search ............... 607/5, 607/7, 8, 14, 27–29, 115, 142, 72; 128/904; 600/561, 508; 324/429
    See application file for complete search history.

(56) References Cited

U.S. PATENT DOCUMENTS

| | | | | |
|---|---|---|---|---|
| 5,014,697 A | * | 5/1991 | Pless et al. | 607/7 |
| 5,511,553 A | * | 4/1996 | Segalowitz | 600/508 |
| 5,593,426 A | * | 1/1997 | Morgan et al. | 607/5 |
| 5,983,137 A | | 11/1999 | Yerkovich | |
| 6,076,018 A | * | 6/2000 | Sturman et al. | 607/72 |
| 6,169,387 B1 | | 1/2001 | Kaib | |
| 6,248,080 B1 | * | 6/2001 | Miesel et al. | 600/561 |
| 6,289,234 B1 | * | 9/2001 | Mueller | 600/410 |
| 6,289,243 B1 | * | 9/2001 | Lin et al. | 607/5 |
| 6,304,779 B1 | * | 10/2001 | Yerkovich | 607/5 |
| 6,366,809 B1 | | 4/2002 | Olson et al. | |
| 6,538,449 B2 | * | 3/2003 | Juncker et al. | 324/429 |
| 2005/0015115 A1 | * | 1/2005 | Sullivan et al. | 607/5 |

OTHER PUBLICATIONS

FR2+ Rechargeable Battery and Charger, Heartstart FR2+ Defibrillator, Philips Medical Systems, 2 pages (2002).
Cardiac Resuscitation System—DF2389R, http://www.bplworld.com/gallery/medical/defib.asp, 3 pages (last printed Aug. 17, 2004).

* cited by examiner

*Primary Examiner*—George Manuel
(74) *Attorney, Agent, or Firm*—Shumaker & Sieffert, P.A.

(57) ABSTRACT

The disclosure describes a medical device that provides an indication of the status of an energy storage device from which it receives power. For example, the medical device may provide an estimate of the number of therapy delivery events available from the medical device based on an estimate of the amount of energy stored in the energy storage device. The medical device may be an external defibrillator, and the therapy delivery events may be defibrillation shocks. Additionally or alternatively, the medical device may indicate an estimated amount of operational time remaining in each of a plurality of monitoring modes based on the estimated amount of stored energy. The energy storage device may be a battery. An energy storage device that itself provides an indication of its status is also disclosed.

75 Claims, 5 Drawing Sheets

INDICATING THE STATUS OF AN ENERGY STORAGE DEVICE OF A MEDICAL DEVICE

TECHNICAL FIELD

The invention relates to medical devices and, more particularly, to medical devices that are powered by an energy storage device.

BACKGROUND

Medical devices used to monitor and/or provide therapy to a patient are often powered by an energy storage device, such as a battery. If the energy storage device becomes depleted, the medical device may no longer be able to perform these functions. In some cases, unexpected depletion of the energy storage device prior to or during use of the medical device to treat a patient may jeopardize the patient's life. For example, external defibrillators may be used to respond to medical emergencies, such as sudden cardiac arrest (SCA). If an energy storage device of an external defibrillator were depleted unexpectedly during treatment of a patient, the patient might not be resuscitated.

Consequently, some medical devices, such as external defibrillators, provide an indication of the status of an associated energy storage device, e.g., a battery charge status indication. For example, some existing medical devices provide an estimate of the percentage or fraction of the full energy storage capacity of the energy storage device that it currently stores. Other existing medical devices indicate an estimated amount of time remaining before the energy storage device is depleted.

SUMMARY

In general, the invention is directed to techniques for providing an indication of the status of an energy storage device, such as a battery, from which a medical device receives power. For example, the medical device may provide an estimate of the number of therapy delivery events available from the medical device based on an estimate of the amount of energy stored in the energy storage device. Additionally or alternatively, the medical device may indicate an estimated amount of operational time remaining in each of a plurality of monitoring modes based on the estimated amount of stored energy.

The medical device may be an external defibrillator, and provide an estimate of the number of defibrillation shocks available from the medical device at a particular defibrillation shock energy level based on an estimate of the amount of energy stored in the energy storage device and the amount of energy consumed by the defibrillator in delivering a shock at the particular energy level. In some embodiments, the external defibrillator may provide an estimate of the number of defibrillation shocks available at each of a plurality of defibrillation shock energy levels. Further, in some embodiments external defibrillator stores a protocol that defines a progression of defibrillation shock energy levels and a number of defibrillation shocks for at least some of the energy levels, and controls defibrillation or provides suggestions for defibrillation to a user for defibrillation according to the stored protocol. For example, automated external defibrillators (AEDs) often store such protocols. In such embodiments, the external defibrillator may provide an estimate of the number of defibrillation shocks according to the protocols that are available from the defibrillator.

Some medical devices provide a plurality of types of patient monitoring, each of which causes the medical device to consume the energy stored by the energy storage device at a particular rate. For example, external defibrillators may provide one or more of electrocardiogram (ECG) monitoring, oxygen saturation monitoring, and temperature monitoring, each of which causes the defibrillator to consume the energy stored by its energy storage device at a relatively low rate. External defibrillators may also provide one or more of non-invasive blood pressure monitoring and partial pressure of carbon dioxide monitoring, each of which causes the defibrillator to consume the energy stored by its energy storage device at a relatively high rate when compared to ECG monitoring, oxygen saturation monitoring, and temperature monitoring.

Further, particular types of monitoring or combinations of these types, e.g., certain monitoring modes, may be used for particular types of patients and emergencies. For example, the combination of ECG monitoring and oxygen saturation monitoring may be a first monitoring mode used for most patients, while a second monitoring mode may additionally include one or more of the other types of patient monitoring and, consequently, consume the energy stored by the energy storage device at a higher rate. A medical device according to the invention may provide an estimate of the remaining operational time in each of a plurality of such monitoring modes based on an estimate of the amount of energy stored by the energy storage device and an estimate of the rate of energy consumption when the medical device operates in the respective monitoring mode.

The medical device may include or be associated with a plurality of energy storage devices. In some embodiments, the medical device provides energy storage device status indications based on an estimate of the total amount of energy stored by the plurality of energy storage devices. In other embodiments, the medical device provides such energy storage device status indications for each of the individual energy storage devices based on an estimate of the amount of energy stored by that energy storage device.

In some embodiments, the energy storage device itself estimates a number of therapy delivery events or operational times in a plurality of monitoring modes, and provides such status indications to the user. The energy storage device may include a user interface, e.g., a display, to provide such status indications to a user. The energy storage device may provide status indications in addition to or as an alternative to provision of status indications by the medical device with which it is associated.

In one embodiment, the invention is directed to a method in which a value that indicates an estimated number of therapy delivery events available from a medical device is stored, an amount of energy stored by an energy storage device of the medical device is periodically estimated, and the stored value is periodically updated based on the estimated amounts of stored energy.

In another embodiment, a device comprises a memory and a processor. The memory stores a value that indicates an estimated number of therapy delivery events available from a medical device. The processor periodically estimates an amount of energy stored by an energy storage device of the medical device, and updates the stored value based on the estimated amount of stored energy.

In another embodiment, the invention is directed to a computer-readable medium containing instructions. The instructions cause a programmable processor to periodically estimate an amount energy stored by an energy storage device of a medical device, and periodically update a value stored in a memory based on the estimated amounts of stored energy, the value indicating an estimated number of therapy delivery events available from the medical device.

In another embodiment, the invention is directed to a method in which a request is received from a user, an amount of energy stored by an energy stored device of a medical device is estimated in response to the request, a number of therapy delivery events available from the medical device is estimated based on the estimated amount of stored energy, and the estimated number of therapy delivery events is presented to the user.

In another embodiment, the invention is directed to a device that comprises a user interface and a processor. The processor receives a request from a user via the user interface, estimates an amount of energy stored by an energy storage device of a medical device in response to the request, estimates a number of therapy delivery events available from the medical device based on the estimated amount of stored energy, and presents the estimated number of therapy delivery events to the user via the user interface.

In another embodiment, the invention is directed to a computer-readable medium containing instructions. The instructions cause a programmable processor to receive a request from a user, estimate an amount of energy stored by an energy storage device of a medical device in response to the request, estimate a number of therapy delivery events available from the medical device based on the estimated amount of stored energy, and present the estimated number of therapy delivery events to the user.

In another embodiment, the invention is directed to a method in which an amount of energy stored by an energy storage device of a medical device that monitors a patient is estimated, a remaining operational time for the medical device in each of a plurality of monitoring modes is estimated based on the estimated amount of stored energy, and the estimated remaining operational times are presented to a user.

In another embodiment, the invention is directed to a device that comprises a user interface and a processor. The processor estimates an amount of energy stored by an energy storage device of a medical device, estimates a remaining operational time for the medical device in each of a plurality of monitoring modes based on the estimated amount of stored energy, and presents the estimated remaining operational times to a user via the user interface.

In another embodiment, the invention is directed to a computer-readable medium containing instructions. The instructions cause a programmable processor to estimate an amount of energy stored by an energy storage device of a medical device, estimate a remaining operational time for the medical device in each of a plurality of monitoring modes based on the estimated amount of stored energy, and present the estimated remaining operational times to a user.

The invention may provide advantages. For example, the energy storage device status indications provided by a medical device or energy storage device according to the invention may allow a user to more easily and accurately appreciate the amount of "use" available from a medical device than is possible with the energy storage device status indications provided by existing medical devices. In particular, indications of the number of therapy delivery events available from a medical device and the remaining operational time available in each of a plurality of monitoring modes may be more informative than an indication of the percentage or fraction of an energy storage device capacity remaining, or a single remaining operational time determined based on an average rate of previous energy consumption.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
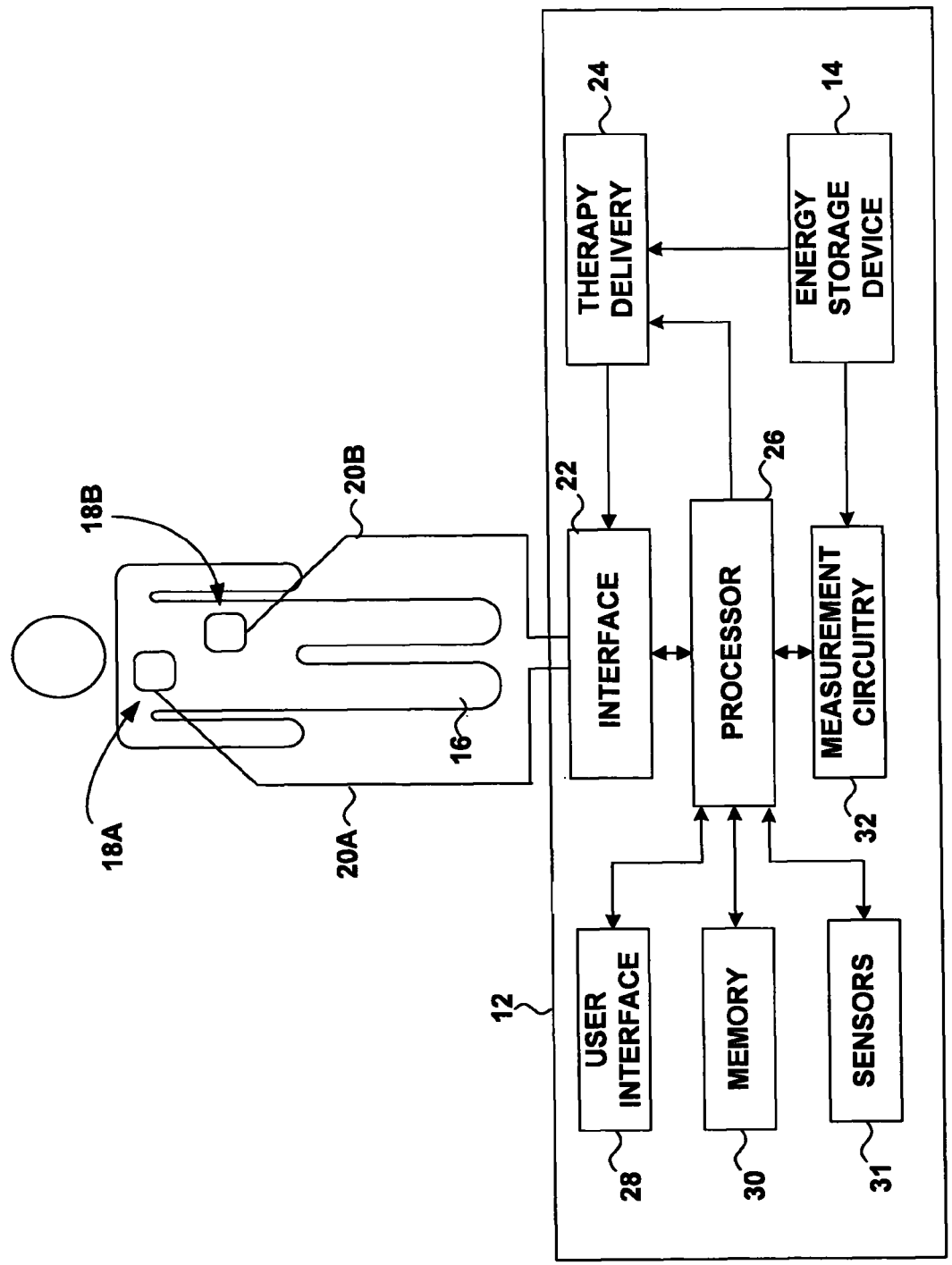
FIG. 1 is a block diagram illustrating an example medical device that provides an indication of the status of an energy storage device from which it receives power.

FIG. 1 is a block diagram illustrating an example medical device that provides an indication of the status of one or more energy storage devices from which it receives power. More particularly, FIG. 1 illustrates an external defibrillator 12 that includes an energy storage device 14, and provides one or more indications of the status of energy storage device 14. As will be described in greater detail below, defibrillator 12 may provide an estimate of the number of therapy delivery events, e.g., defibrillation shocks, available from defibrillator 12 based on an estimate of the amount of energy stored in energy storage device 14. Additionally or alternatively, defibrillator 12 may indicate an estimated amount of operational time remaining in each of a plurality of monitoring modes of defibrillator 12 based on the estimated amount of stored energy. Energy storage device status indications such as these may allow a user to more easily and accurately appreciate the amount of "use" available from defibrillator 12 than is possible with the energy storage device status indications provided by existing defibrillators.

In FIG. 1, defibrillator 12 is shown coupled to a patient 16 by electrodes 18A and 18B (collectively "electrodes 18"). Electrodes 18 may include hand-held electrode paddles or adhesive electrode pads placed on the skin of patient 16. Electrodes 18 are coupled to defibrillator 12 via respective conductors 20A and 20B (collectively "conductors 20") and an interface 22. In a typical application, interface 22 includes a receptacle, and conductors 20 plug into the receptacle.

Interface 22 includes a switch (not shown in FIG. 1) that, when activated, couples therapy delivery circuitry 24 to electrodes 18 for delivery of energy to patient 16 via electrodes 18 in the form of a defibrillation shock. The switch may be of conventional design and may be formed, for example, of electrically operated relays. Alternatively, the switch may comprise an arrangement of solid-state devices such as silicon-controlled rectifiers or insulated gate bipolar transistors.

Therapy delivery circuitry 24 includes components, such as one or more capacitors, that store the energy to be delivered to patient 16 as a defibrillation shock. Before a defibrillation shock may be delivered to patient 16, these energy storage components are charged by charging circuitry, such as a flyback charger, that transfers energy from energy storage device 14 to the components. A processor 26 directs the charging circuitry to charge the energy storage components to a selected voltage level that is determined based on a selected energy level for the defibrillation shock to be delivered to patient 16.

Defibrillator 12 may be a manual defibrillator or an AED. Where defibrillator 12 is a manual defibrillator, a caregiver using defibrillator 12 may select an energy level for each defibrillation shock delivered to patient 12. Processor 26 may receive the selection made by the caregiver via a user interface 28, which may include input devices, such as a keypad and various buttons or dials, and output devices, such as various indicator lights, a cathode ray tube (CRT), light emitting diode (LED), or liquid crystal display (LCD) screen, and a speaker. Where defibrillator 12 is an AED, processor 26 may select an energy level based on protocol stored in a memory 30 and the number of defibrillation shocks already delivered to patient 16. The protocol may define a preprogrammed progression of energy levels and numbers of shocks to be delivered at each energy level.

When the energy stored by therapy delivery circuitry 24 reaches the desired energy level, processor 26 controls user interface 28 to provide an indication to the caregiver that defibrillator 12 is ready to deliver a defibrillation shock to patient 16, such as an indicator light or a voice prompt. The defibrillation shock may be delivered manually or automatically. Where the defibrillation shock is delivered manually, the caregiver may direct processor 26 to deliver the defibrillation shock via user interface 28 by, for example, pressing a button. In either case, processor 26 activates the switches of interface 22 to electrically connect therapy delivery circuit 24 to electrodes 18, and thereby deliver the defibrillation shock to patient 16.

Processor 26 may perform other functions as well, such as monitoring electrical activity of the heart of patient 16 sensed via electrodes 18. Processor 26 may determine whether the heart of patient 16 is fibrillating based upon the sensed electrical activity in order to determine whether a defibrillation shock should be delivered to patient 16. Where a defibrillation shock has already been delivered, processor 26 may evaluate the efficacy of the delivered defibrillation shock by determining if the heart is still fibrillating in order to determine whether an additional defibrillation shock is warranted. Processor 26 may automatically deliver defibrillation shocks based on these determinations, or may advise the caregiver of these determinations via user interface 28.

Processor 26 may display an electrocardiogram (ECG) that reflects the sensed electrical activity via user interface 28. Further, processor 26 may control delivery of other types of therapy to patient 16 via electrodes 18, such as cardioversion or pacing therapy. Where defibrillator 12 is more fully featured, e.g., a manual paramedic or hospital defibrillator, defibrillator 12 may also include or be connected to additional sensors 31 that are coupled to processor 26, such as sensors to measure blood oxygen saturation, temperature, blood pressure, and the amount of carbon dioxide in the air inhaled or exhaled by patient 16. Sensors 31 may be coupled to processor 26 via any of a variety of known types of circuitry for conditioning, sampling and/or pre-processing the signals output by such sensors.

Energy storage device 14 may comprise one or more batteries, such as lead acid or lithium ion batteries. In other embodiments, energy storage device 14 comprises one or more capacitors or supercapacitors. Energy storage device 14 may be rechargeable. Further, energy storage device 14 may be removable from defibrillator 12 for recharging or replacement although, in some embodiments, energy storage device 14 may be recharged while still coupled to defibrillator 12. Although not illustrated in FIG. 1, energy storage device 14 may provide energy for substantially all of the components and functions of defibrillator 12 in addition to therapy delivery circuitry 24 and delivery of defibrillation shocks.

Processor 26 estimates the amount of energy currently stored by energy storage device 14 in order to provide an indication of the status of energy storage device 14. Processor 26 may employ any of a variety of known techniques to estimate the stored energy. For example, processor 26 may estimate the amount of energy currently stored based on a known capacity of energy storage device 14, and an estimate of the amount of energy consumed since the last time energy storage device 14 was charged to the capacity.

In some embodiments, processor 26 estimates the amount of consumed energy by monitoring the length of time that defibrillator 12 was in various modes of operation, the number of defibrillation shocks delivered and their energy level, and the like since the last time energy storage device 14 was charged to the capacity. Memory 30 may store values for the rate that defibrillator 12 consumes energy in various operational modes, the amount of energy consumed by defibrillation shocks and other therapies at various energy levels, and a value for the known capacity of energy storage device 14. Processor 26 may use the values derived from monitoring the use of defibrillator and the values stored in memory 30 to estimate the amount of energy currently stored by energy storage device 14.

In other embodiments, measurement circuitry 32 may continuously or periodically measure the current drain from energy storage device 14, and determine an estimated average current drain during the period since the last time energy storage device 14 was charged to full capacity. Processor 26 may estimate the energy consumed from energy storage device 14 during this period by, for example, applying an equation or look-up table stored in memory 30 to the estimated average current drain. Processor 26 may then estimate the amount of energy stored by the energy storage device 14 based on the estimated amount of energy consumed and a full capacity value for the energy storage device stored in memory 30.

In still other embodiments, measurement circuitry 32 may measure one or more parameters of energy storage device 14, such voltage, discharge current, impedance, or temperature, and processor 26 may estimate the stored energy directly, i.e., without reference to the capacity of energy storage device 14, based on the measured parameter values. Processor 26 may estimate the amount of energy stored by energy storage device 14 by, for example, applying an equation or look-up table stored in memory 30 to the measured parameter values.

In some embodiments, processor 26 estimates the number of defibrillation shocks available defibrillator 12 at a particular defibrillation shock energy level based on the estimated amount of energy stored in the energy storage device and the amount of energy consumed by the defibrillator in delivering a shock at the particular energy level. A value for the amount of energy consumed by defibrillator 12 in delivering a shock at the particular energy level may be stored in memory 30.

Processor 26 may estimate the number of defibrillation shocks available at each of a plurality of defibrillation shock energy levels in this manner. Further, in embodiments in which memory 30 stores a protocol that defines a progression of defibrillation shock energy levels and a number of defibrillation shocks for at least some of the energy levels, processor 26 may estimate of the number of defibrillation shocks according to the protocol that are available from the defibrillator. In particular, processor 26 may determine the number of shocks available according to a protocol based on the energy levels and numbers of shocks defined by the protocol, values for the amount of energy consumed by defibrillator 12 in delivering shocks at particular energy levels stored in memory 30, and the estimated amount of stored energy.

As described above, defibrillator 12 may provide one or more of ECG monitoring, oxygen saturation monitoring, and temperature monitoring, non-invasive blood pressure monitoring and partial pressure of carbon dioxide monitoring. Each of these types of monitoring cause defibrillator 12 to consume energy from energy storage device 14 at a different rate. For example, non-invasive blood pressure monitoring and partial pressure of carbon dioxide monitoring cause defibrillator 12 to consume the energy stored by energy storage device 14 at a relatively high rate when compared to ECG monitoring, oxygen saturation monitoring, and temperature monitoring. Further, certain ones or combinations of these types of monitoring, i.e., certain monitoring modes, may be commonly used for particular types of patients and emergencies. For example, the combination of ECG monitoring and oxygen saturation monitoring may be a first monitoring mode used for most patients and emergencies, while a second monitoring mode used for particular patients or emergencies may additionally include one or more of the other types of patient monitoring, such as non-invasive blood pressure monitoring.

In some embodiments, processor 26 may estimate the amounts of operational time remaining in each of a plurality of monitoring modes, in addition to or as an alternative to estimating numbers of defibrillation shocks available, based on the estimated amount of stored energy. Memory 30 may store a rate of energy consumption value for each of the monitoring modes, and processor 26 may estimate the remaining operational times based rate of energy consumption values and the estimated amount of energy stored by energy storage device. In some embodiments, a user may configure the monitoring modes, e.g., select which types of monitoring are included within each of a plurality of modes, via user interface 28. In such embodiments, processor 26 may determine the rate of energy consumption for a mode based on rates of energy consumption stored in memory for each type of monitoring that is part of the monitoring mode.

In some embodiments, processor 26 periodically estimates the amount of energy stored within energy storage device 14, and estimates one or both of numbers of defibrillation shocks available and remaining operational times based on the estimated amount of stored energy. In such embodiments, processor 26 may periodically update values for the estimated numbers of available defibrillation shocks and estimated remaining operational times stored within memory 30. Processor 26 may present the currently stored values to a user via user interface 28, e.g., via a display of defibrillator 12, either continuously or in response to a request received from the user via the user interface. In other embodiments, processor 26 estimates the amount of energy stored within energy storage device 14, estimates numbers of defibrillation shocks available or remaining operational times, and presents the estimated numbers or time to a user via user interface 28 in response to a request received from the user via the user interface.

In some embodiments, defibrillator 12 is associated with a plurality of energy storage devices 14, such as a primary energy storage device and backup energy storage device. The plurality of energy storage devices 14 may be simultaneously coupled to, e.g., carried by defibrillator 12, or only one of the energy storage devices may be coupled to defibrillator 12 at a given time. Where defibrillator 12 is coupled to a plurality of energy storage devices 14 at the same time, defibrillator 12 may draw power from one or more of the plurality of energy storage devices at any give time.

In embodiments in which defibrillator 12 is associated with a plurality of energy storage devices 14, processor 26 may estimate the amount of energy stored by each of the energy storage devices. When they are simultaneously coupled to defibrillator 12, processor 26 may estimate the amount of energy stored by each of a plurality of energy storage devices 14 using any of the techniques described above. When energy storage devices 14 are not simultaneously coupled to defibrillator 12, processor 26 may assume that any non-coupled energy storage devices are at full capacity.

In some embodiments, processor 26 estimates a total amount of energy stored by the plurality of energy storage devices 14 based on the estimated amounts of energy stored by each of the devices, and estimates numbers of defibrillation shocks available or remaining operational times based on the total amount of stored energy. In other embodiments, processor 26 estimates numbers of defibrillation shocks available and remaining operational times for each of the plurality of energy storage devices based on the estimated amount of energy stored by that energy storage device 18. In such embodiments, the estimated numbers of defibrillation shocks available and remaining operational times for a particular energy storage device 14 represent the numbers of defibrillation shocks and operational times that would be available when defibrillator 12 is powered by that energy storage device 14.

Processor 26 may, for example, include one or more of a microprocessor, digital signal processor (DSP), application specific integrated circuit (ASIC), field programmable gate array (FPGA), or other logic circuitry. In addition to various values, look-up tables, or equations described above, memory 30 may include program instructions that cause processor 26 to perform the functions attributed to processor 26 herein. Memory 30 may include any of a variety of solid state, magnetic or optical media, such as random access memory (RAM), read-only memory (ROM), CD-ROM, magnetic disk, electrically erasable programmable ROM (EEPROM), or flash memory.

Figure 2:
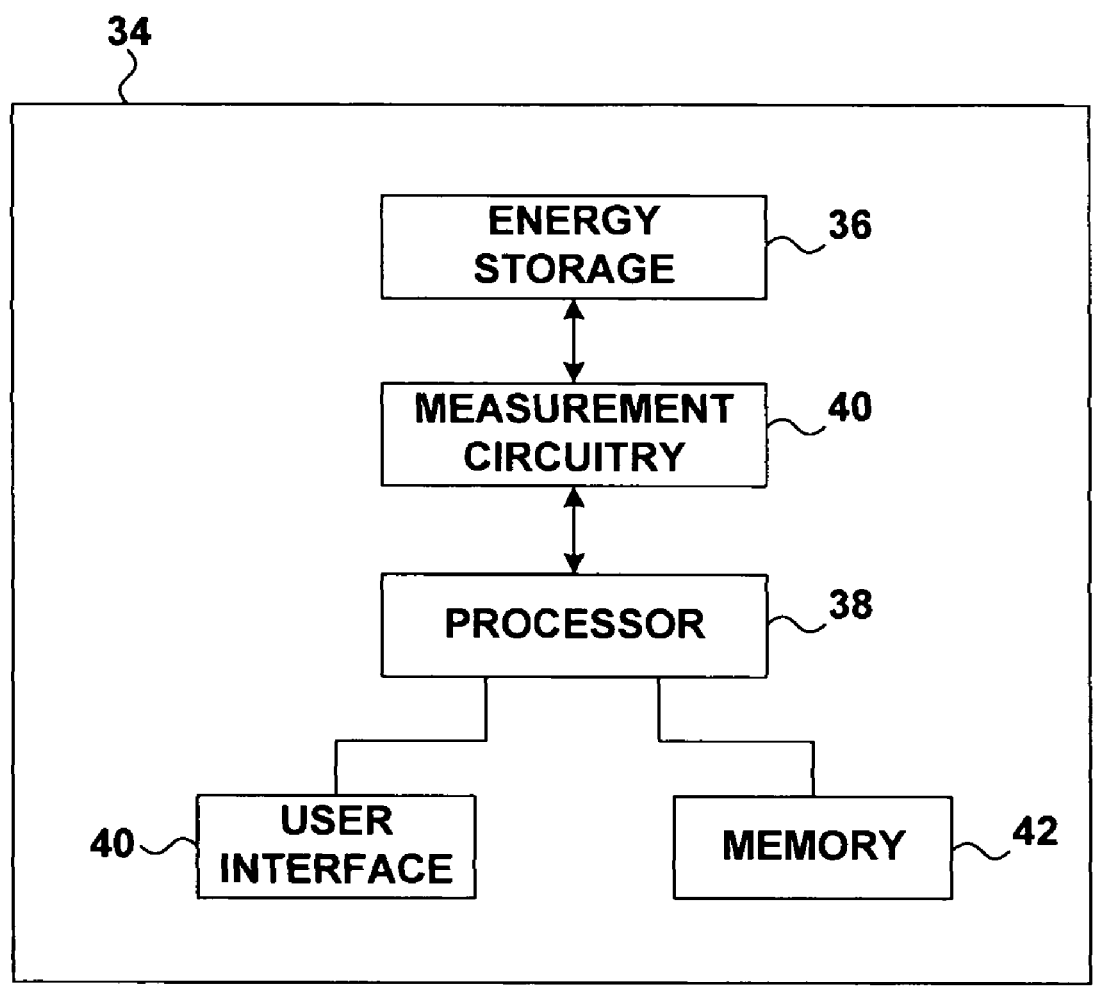
FIG. 2 is a block diagram illustrating an example energy storage device that provides an indication of its status.

FIG. 2 is a block diagram illustrating an example energy storage device 34 that provides an indication of its status. Energy storage device 34 may provide an indication of its status in addition to or as an alternative to status indications provided by a defibrillator 12 to which it provides power. Energy storage device 34 may be substantially similar to energy storage device 14 described above with reference to FIG. 1, but additionally includes various modules or circuitry for provision of a status indication to user.

In particular, in addition to an energy storage element 36, e.g., one or more chemical cells, energy storage device 34 may include a processor 38, measurement circuitry 40, a user interface 42 and a memory 44. Processor 38 may interact with one or more of measurement circuitry 40, user interface 42 and memory 44 to estimate the amount of energy stored by energy storage element 36, estimate numbers of defibrillation shocks and/or remaining operational times based on the estimated amount of stored energy, and present the estimated numbers of defibrillation shocks and/or remaining operational times to a user. Processor 38 may interact with the one or more of measurement circuitry 40, user interface 42 and memory 44 in substantially the same the manner described above with reference to processor 26, user interface 28, memory 30 and measurement circuitry 32 of FIG. 1.

User interface 42 may include display, such as a light emitting diode (LED) or liquid crystal display (LCD) screen, for presentation of the estimated numbers of defibrillation shocks and/or remaining operational times. User interface 42 may also include input devices, such as a keypad or one or more buttons, to allow a user to request such status information. In some embodiments, the display provided by user interface 42 may be inactive until processor 38 receives a request from a user via the user interface.

Processor 38 may, for example, include one or more of a microprocessor, digital signal processor (DSP), application specific integrated circuit (ASIC), field programmable gate array (FPGA), or other logic circuitry. Memory 42 may store the various values, look-up tables, or equations described above with reference to memory 30 of defibrillator 14 to enable processor 38 to estimate the amount of energy stored by energy storage element 36, and estimate numbers of defibrillation shocks and/or remaining operational times based on the estimated amount of stored energy. Memory 42 may also include program instructions that cause processor 38 to perform the functions attributed to processor 38 herein. Memory 42 may include any of a variety of solid-state media, such as RAM, ROM, EEPROM, or flash memory.

Figure 3:
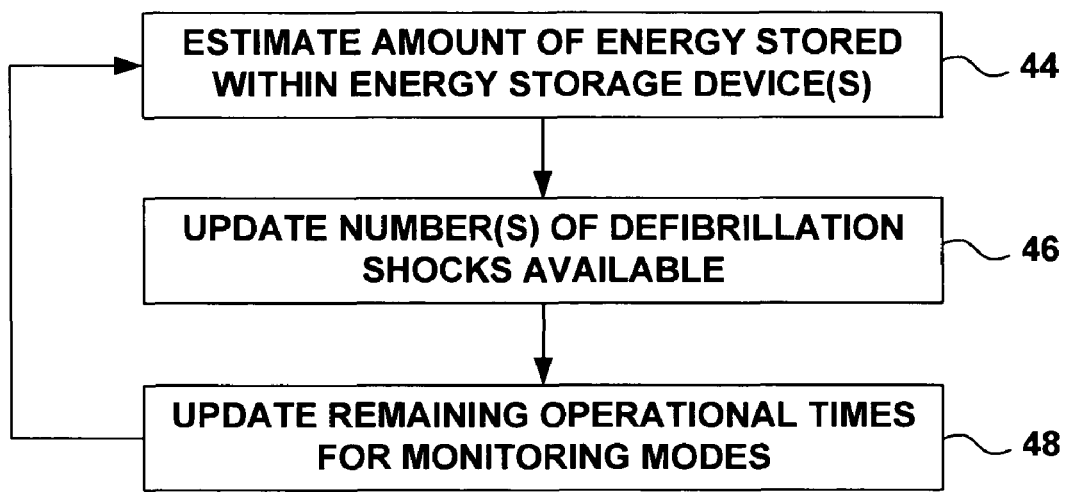
FIG. 3 is a flowchart illustrating an example method for indicating the status of one or more energy storage devices.

FIG. 3 is a flowchart illustrating an example method for indicating the status of an energy storage device. Although described in context of a defibrillator 12 that indicates the status of an energy storage devices 14 from which it receives power, the method illustrated by FIG. 3 may also be performed by an energy storage device 34 that provides an indication of its own status. Further, although the example method illustrates indication of the status of a single energy storage device 14 of the defibrillator 12, in other embodiments a defibrillator indicates the status of a plurality of energy storage devices 14, as described above.

FIG. 3 illustrates a method in which a defibrillator 12 periodically estimates the amount of energy stored by an energy storage device 14, and updates estimated numbers of defibrillation shocks available and estimated remaining operational times based on the estimated amounts of stored energy. Memory 30 of defibrillator 14 stores values indicating estimated numbers of defibrillation shocks available at each of one or more defibrillation shock energy levels, and estimated remaining operational times in each of a plurality of monitoring modes. Processor 26 presents the values currently stored in memory 30 to a user via user interface 28, e.g., via a display, either continuously or in response to receipt of a request from a user via the user interface.

According to the example method, defibrillator 12, and more particularly processor 26, estimates the amount of energy stored by the energy storage device 14 using any of the techniques described above (44). Processor 26 estimates the number of defibrillation shocks available at each of one or more defibrillation shock energy levels based on the estimated amount of stored energy and an amount of energy consumed by defibrillator 12 per defibrillation shock at that energy level, and updates the one or more corresponding values stored in memory 30 to reflect the newly estimated numbers (46). In some embodiments, processor 26 additionally or alternatively estimates a number of defibrillation shocks available according to a protocol, as described above, and updates a corresponding value stored in memory.

Processor 26 also estimates the remaining operational time in each of a plurality of monitoring modes based on the estimated amount of stored energy and a rate of energy consumption by defibrillator 12 when operating in that monitoring mode, and updates corresponding values indicating remaining operational times stored in memory 30 to reflect the newly estimated remaining operational times (48). For example, processor 26 may estimate a first remaining operational time for a first monitoring mode that includes at least one of electrocardiogram monitoring, oxygen saturation monitoring, or temperature monitoring, and a second remaining operational time for a second monitoring mode that includes at least one of non-invasive blood pressure monitoring or partial pressure of carbon dioxide monitoring. As discussed above, processor 26 may estimate stored energy, and update estimated available shock numbers and remaining operational times (44-48) periodically.

Figure 4:
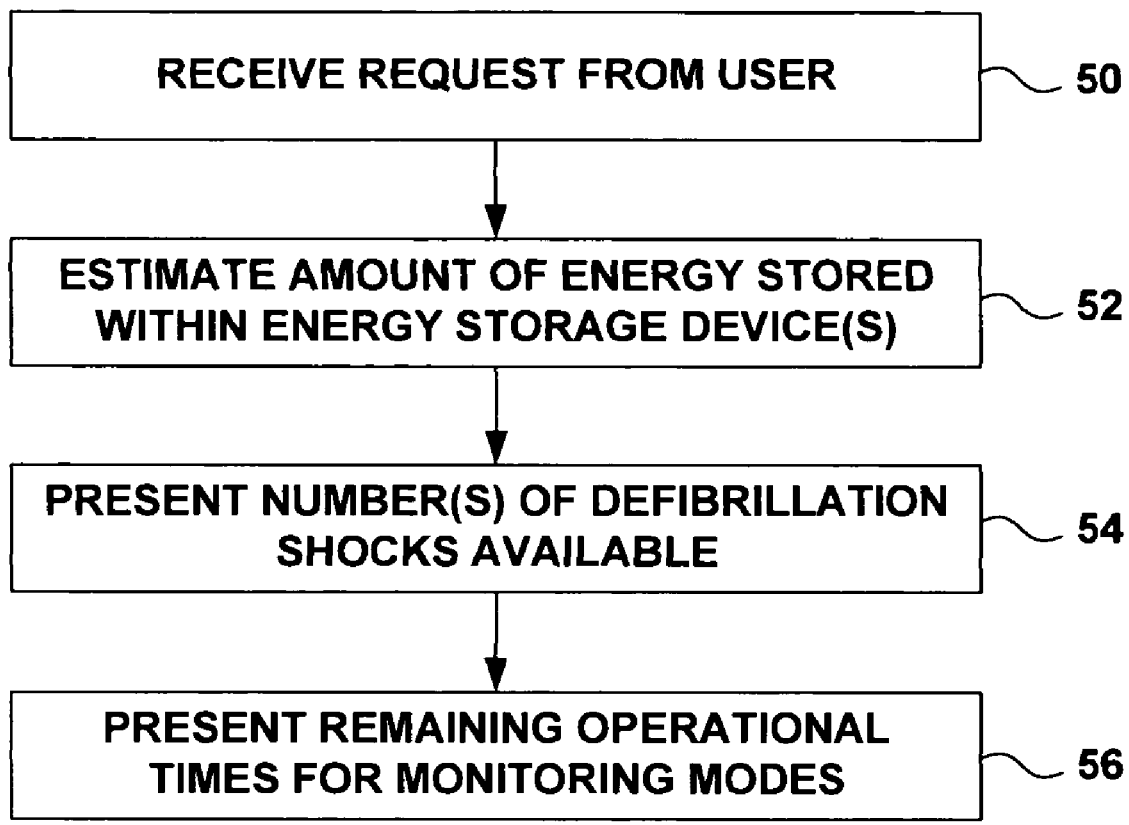
FIG. 4 is a flowchart illustrating another example method for indicating the status of an energy storage device.

FIG. 4 is a flowchart illustrating another example method for indicating the status of an energy storage device. Although described in context of a defibrillator 12 that indicates the status of an energy storage devices 14 from which it receives power, the method illustrated by FIG. 4 may also be performed by an energy storage device 34 that provides an indication of its own status. Further, although the example method illustrates indication of the status of a single energy storage device 14 of the defibrillator 12, in other embodiments a defibrillator indicates the status of a plurality of energy storage devices 14, as described above.

FIG. 4 illustrates a method in which the defibrillator 12 provides an indication of the status of the energy storage device 14 in response to receipt of a request from a user. According to the method, processor 26 receives a request for an indication of the status of the energy storage device 14 from a user via a user interface 28 (50). Processor 26 then estimates the amount of energy stored by the energy storage device 14 in response to the user request using any of the techniques described above (52).

Processor 26 estimates the number of defibrillation shocks available at each of one or more defibrillation shock energy levels based on the estimated amount of stored energy and an amount of energy consumed by defibrillator 12 per defibrillation shock at that energy level, and updates the one or more corresponding values stored in memory 30 to reflect the newly estimated numbers (54). In some embodiments, processor 26 additionally or alternatively estimates a number of defibrillation shocks available according to a protocol, as described above, and updates a corresponding value stored in memory. Processor 26 also estimates the remaining operational time in each of a plurality of monitoring modes based on the estimated amount of stored energy and a rate of energy consumption by defibrillator 12 when operating in that monitoring mode, and updates corresponding values indicating remaining operational times stored in memory 30 to reflect the newly estimated remaining operational times (56). For example, processor 26 may estimate a first remaining operational time for a first monitoring mode that includes at least one of electrocardiogram monitoring, oxygen saturation monitoring, or temperature monitoring, and a second remaining operational time for a second monitoring mode that includes at least one of non-invasive blood pressure monitoring or partial pressure of carbon dioxide monitoring.

Figure 5:
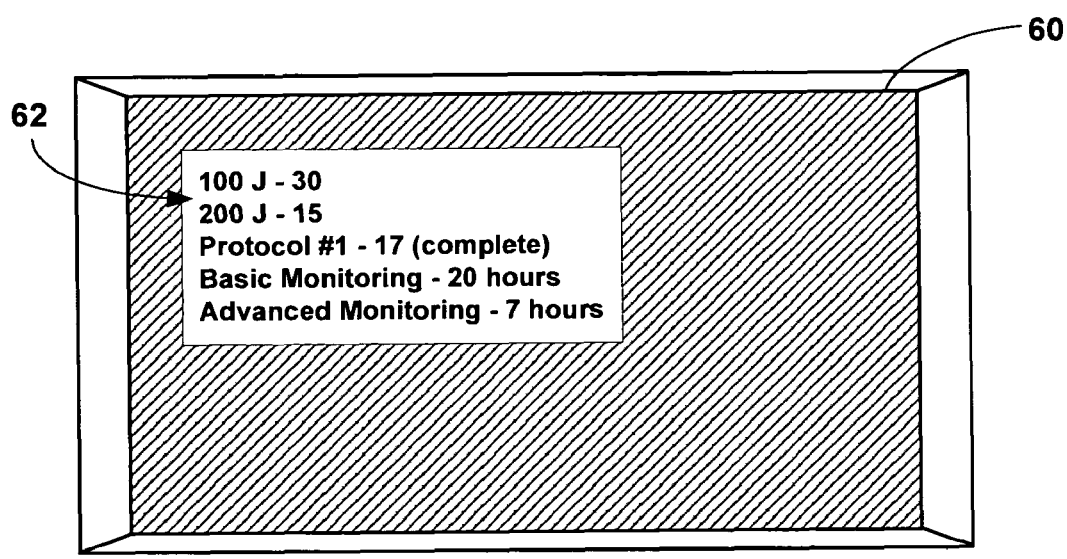
FIG. 5 is a conceptual diagram illustrating a display of a medical device that provides an indication of the status of an energy storage device from which it receives power.

FIG. 5 is a conceptual diagram illustrating a display 60, which may be a component of user interface 28 of defibrillator 12. More particularly, FIG. 5 illustrates an example indication 62 of the status of energy storage device 14 that processor 26 may present via display 60. Through the illustrated indication 62, processor 26 presents estimated numbers of defibrillator shocks available at two example defibrillation shock energy levels and according to a protocol, and estimated remaining operational times for two example monitoring modes. As indicated above, processor 26 may provide a continuous indication via display 60, or in response to a user request. In other embodiments, display 60 may be a component of user interface 40 of an energy storage device 34 that indicates its status, and a processor 38 of the energy storage device 34 may present the indication 62 via the display 60. For example, a battery may include a built-in display 60 to present the status of that battery.

Various embodiments of the invention have been described. However, one skilled in the art will appreciate that various modifications may be made to the described embodiments without departing from the scope of the invention. For example, although described herein in the context of an external defibrillator, a medical device according to the invention may be any implantable or external medical device, such as a pacemaker, a pacemaker with cardioversion and defibrillation capabilities, a neurostimulator, a muscular stimulator, a gastrointestinal stimulator, a urological stimulator, implantable pump, or a monitoring device, such as an implantable loop recorder.

Further, although described herein in the context of defibrillation shocks, therapy delivery events are not so limited. Therapy delivery events may be, for example, any type electrical stimulation event or pump activation event. Moreover, monitoring modes are not limited to those described herein in the context of an external defibrillator. For example, an implantable pacemaker may provide a variety of monitoring modes, each with a different rate of energy consumption, such as different monitoring modes associated with demand pacing, rate-responsive pacing, and pacing with tachyarrhythmia detection. These and other embodiments are within the scope of the following claims.

The invention claimed is:

1. A method comprising:
storing, by a medical device that delivers therapy to a patient, a value that indicates an estimated number of therapy delivery events available from the medical device;
periodically estimating an amount of energy stored by an energy storage device of the medical device;
periodically estimating a number of therapy delivery events available from the medical device based on the estimated amounts of stored energy to produce updated estimates;
periodically updating the stored value based on the updated estimates; and
presenting the stored value to a user.

2. The method of claim 1, wherein the medical device comprises an external defibrillator, and storing a value that indicates an estimated number of therapy delivery events comprises storing a value that indicates an estimated number of defibrillation shocks.

3. The method of claim 2,
wherein storing a value that indicates an estimated number of defibrillation shocks comprises storing a plurality of values, each of the values indicating an estimated number of defibrillation shocks available at a respective one of a plurality of energy levels, and
wherein periodically updating the stored value comprises periodically updating each of the stored values based on the estimated amounts of stored energy.

4. The method of claim 2, wherein the external defibrillator stores a protocol that defines a progression of defibrillation shock energy levels and a number of defibrillation shocks for at least some of the energy levels, and storing a value that indicates an estimated number of defibrillation shocks available comprises storing a value that indicates an estimated number of defibrillation shocks according to the protocol that are available from the defibrillator.

5. The method of claim 1, wherein periodically estimating an amount of energy stored by an energy storage device of the medical device comprises periodically estimating a total amount of energy stored by a plurality of energy storage devices of the medical device.

6. The method of claim 1,
wherein storing a value that indicates an estimated number of therapy delivery events available from a medical device comprises storing a plurality of values, each of the values associated with a respective one of a plurality of energy storage devices of the medical device,
wherein periodically estimating an amount of energy stored by an energy storage device of the medical device comprises periodically estimating an amount of energy stored by each of the plurality of energy storage devices, and
wherein periodically updating the stored value based on the estimated amounts of energy comprises periodically updating each of the stored values based on the estimated amounts of energy stored by the respective one of the energy storage devices.

7. The method of claim 1, further comprising displaying the stored value.

8. The method of claim 7, wherein displaying the stored value comprises substantially continuously displaying the stored value via a display of the medical device when the medical device is operational.

9. The method of claim 7, wherein displaying the stored value comprises displaying the stored value via a display of the energy storage device.

10. The method of claim 7, wherein displaying the stored value comprises:
receiving a command from the user via a user interface of the medical device; and
displaying the stored value via the display of the medical device in response to the command.

11. The method of claim 1, wherein periodically estimating an amount of energy stored by an energy storage device, comprises periodically estimating an amount of energy stored by a battery.

12. A device comprising:
a memory to store a value that indicates an estimated number of therapy delivery events available from a medical device that delivers therapy to a patient; and
a processor configured to periodically estimate an amount of energy stored by an energy storage device of a medical device, periodically estimate a number of therapy delivery events available from the medical device based on the estimated amounts of stored energy to produce updated estimates, and update the stored value based on the updated estimates.

13. The device of claim 12, wherein the medical device comprises an external defibrillator, and the value stored by the memory indicates an estimated number of defibrillation shocks available from the external defibrillator.

14. The device of claim 13, wherein the memory stores a plurality of values, each of the values indicating an estimated number of defibrillation shocks available at a respective one of a plurality of energy levels, and the processor updates each of the stored values based on the estimated amount of stored energy.

15. The device of claim 13, wherein the external defibrillator stores a protocol that defines a progression of defibrillation shock energy levels and a number of defibrillation shocks for at least some of the energy levels, and the value stored by the memory indicates an estimated number of defibrillation shocks according to the protocol that are available from the defibrillator.

16. The device of claim 12, wherein the processor periodically estimates a total amount of energy stored by a plurality of energy storage devices of the medical device, and updates the stored value based on the estimated total amount of stored energy.

17. The device of claim 12,
wherein the memory stores a plurality of values, each of the values associated with a respective one of a plurality of energy storage devices of the medical device and indicating an estimated number of therapy delivery events available from the medical device when the medical device is powered by the respective one of the energy storage devices, and
wherein the processor periodically estimates an amount of energy storage by each of a plurality energy storage devices of the medical device, and updates each of the stored values based on the estimated amount of energy stored by the respective one of the energy storage devices.

18. The device of claim 12, further comprising a display, wherein the processor displays the stored value via the display.

19. The device of claim 18, wherein processor displays the stored value substantially continuously via the display when the device is operational.

20. The device of claim 18, further comprising a user interface, wherein the processor receives a command from a user via the user interface, and displays the stored value via the display in response to the command.

21. The device of claim 12, wherein the device comprises the medical device.

22. The device of claim 21, wherein the medical device comprises an external defibrillator.

23. The device of claim 12, wherein the energy storage device comprises a battery.

24. The device of claim 12, wherein the device comprises the energy storage device.

25. A non-transitory computer-readable medium comprising instructions that cause a programmable processor to:
periodically estimate an amount of energy stored by an energy storage device of a medical device that delivers therapy to a patient;
periodically estimate a number of therapy delivery events available from the medical device based on the estimated amounts of stored energy to produce updated estimates; and
periodically update a value stored in a memory based on the updated estimates, the value indicating an estimated number of therapy delivery events available from the medical device.

26. The computer-readable medium of claim 25, wherein the medical device comprises an external defibrillator, and the instructions that cause a programmable processor to periodically update a value that indicates an estimated number of therapy delivery events comprise instructions that cause a programmable processor to periodically update a value that indicates an estimated number of defibrillation shocks available from the external defibrillator.

27. The computer-readable medium of claim 26, wherein the memory stores a plurality values, each of the values indicating an estimated number of defibrillation shocks available at a respective one of a plurality of energy levels, and the instructions that cause a programmable processor to periodically update a value comprise instructions that cause a programmable processor to periodically update each of the stored values based on the estimated amounts of stored energy.

28. The computer-readable medium of claim 26, wherein the external defibrillator stores a protocol that defines a progression of defibrillation shock energy levels and a number of defibrillation shocks for at least some of the energy levels, and the instructions that cause a programmable processor to periodically update a value comprise instructions that cause a programmable processor to periodically update a value that indicates an estimated number of defibrillation shocks according to the protocol that are available from the defibrillator.

29. The computer-readable medium of claim 25, further comprising instructions that cause a programmable processor to periodically estimate a total amount of energy stored by the plurality of energy storage devices of the medical device, wherein the instructions that cause a programmable processor to periodically update a value comprise instructions that cause a programmable processor to periodically update the value based on the estimated total amounts of stored energy.

30. The computer-readable medium of claim 25,
wherein the memory stores a plurality of values, each of the values associated with a respective one of a plurality of energy storage devices of the medical device and indicating an estimated number of therapy delivery events available from a medical device when the medical device is powered by the respective one of the energy storage devices, and
the computer-readable medium further comprises instructions that cause a programmable processor to:
periodically estimate an amount of energy stored by each of energy storage devices; and
periodically update each of the stored values based on the estimated amounts of energy stored by the respective one of the energy storage devices.

31. The computer-readable medium of claim 25, further comprising instructions that cause a programmable processor to display the stored value via a display.

32. A method comprising:
receiving a request from a user;
in response to the request estimating an amount of energy stored by an energy storage device of a medical device that delivers therapy to a patient;
estimating, by the medical device, a number of therapy delivery events available from the medical device based on the estimated amount of energy stored by the energy storage device; and
presenting the estimated number of therapy delivery events to the user.

33. The method of claim 32, wherein the medical device comprises an external defibrillator, and estimating a number of therapy delivery events comprises estimating a number of defibrillation shocks.

34. The method of claim 33, wherein estimating a number of defibrillation shocks comprises estimating a number of defibrillation shocks available from the external defibrillator at each of a plurality of energy levels.

35. The method of claim 33, wherein the external defibrillator stores a protocol that defines a progression of defibrillation shock energy levels and a number of defibrillation shocks for at least some of the energy levels, and estimating a number of defibrillation shocks available comprises estimating a number of defibrillation shocks according to the protocol that are available from the defibrillator.

36. The method of claim 32, wherein estimating an amount of energy stored by an energy storage device of a medical device comprises estimating a total amount of energy stored by a plurality of energy storage devices of the medical device, and estimating a number of therapy delivery events comprises estimating the number of therapy delivery events based on the estimated total amount of stored energy.

37. The method of claim 32, wherein estimating an amount of energy stored by an energy storage device of a medical device comprises estimating an amount of energy stored by each of a plurality of energy storage devices of the medical device, and estimating a number of therapy delivery events comprises, for each of the energy storage devices, estimating a number of therapy delivery events available from the medical device when the medical device is powered by the energy storage device based on the estimated amount of energy stored by the energy storage device.

38. The method of claim 32,
wherein receiving a request from a user comprises receiving the request via a user interface of the medical device, and
presenting the estimated number of therapy delivery events comprises displaying the estimated number of therapy delivery events via a display of the medical device.

39. The method of claim 32, wherein estimating an amount of energy stored by an energy storage device comprises estimating an amount of energy stored by a battery.

40. A device comprising:
a user interface; and
a processor configured to receive a request from a user via the user interface, estimate an amount of energy stored by an energy storage device of a medical device that delivers therapy to a patient in response to the request, estimate a number of therapy delivery events available from the medical device based on the estimated amount of stored energy, and present the estimated number of therapy delivery events to the user via the user interface.

41. The device of claim 40,
wherein the medical device comprises an external defibrillator, and
wherein the processor estimates a number of defibrillation shocks available from the external defibrillator based on the estimated amount of energy, and presents the estimated number of defibrillation shocks to the user.

42. The device of claim 41, wherein the processor estimates a number of defibrillation shocks available from the external defibrillator at each of a plurality of energy levels based on the estimated amount of stored energy, and presents the estimated number of defibrillation shocks available at each of the energy levels to the user.

43. The device of claim 41,
wherein the external defibrillator stores a protocol that defines a progression of defibrillation shock energy levels and a number of defibrillation shocks for at least some of the energy levels, and
wherein the processor estimates a number of defibrillation shocks according to the protocol that are available from the defibrillator based on the estimated amount of stored energy, and presents the estimated number of defibrillation shocks according to the protocol to the user.

44. The device of claim 40, wherein the processor estimates a total amount of energy stored by a plurality of energy storage devices of the medical device, and estimates the number of therapy events based on the estimated total amount of stored energy.

45. The device of claim 40, wherein the processor estimates an amount of energy stored by each of a plurality of energy storage devices of the medical device, and, for each of the energy storage devices, estimates a number of therapy delivery events available from the medical device when the medical device is powered by the energy storage device based on the estimated amount of energy stored by the energy storage device.

46. The device of claim 40, wherein the device comprises the medical device.

47. The device of claim 46, wherein the medical device comprises an external defibrillator.

48. The device of claim 40, wherein the device comprises the energy storage device.

49. The device of claim 40, wherein the energy storage device comprises a battery.

50. A non-transitory computer-readable medium comprising instructions that cause a programmable processor to:
receive a request from a user;
estimate an amount of energy stored by an energy storage device of a medical device that delivers therapy to the patient in response to the request;
estimate a number of therapy delivery events available from the medical device based on the estimated amount of stored energy; and
present the estimated number of therapy delivery events to the user.

51. The computer-readable medium of claim 50, wherein the medical device comprises an external defibrillator, and the instructions that cause a programmable processor to estimate a number of therapy delivery events comprise instructions that cause a programmable processor to estimate a number of defibrillation shocks available from the external defibrillator based on the estimated amount of stored energy.

52. The computer-readable medium of claim 51, wherein the instructions that cause a programmable processor to estimate a number of defibrillation shocks comprise instructions that cause a programmable processor to estimate a number of defibrillation shocks available from the external defibrillator at each of a plurality of energy levels based on the estimated amount of stored energy.

53. The computer-readable medium of claim 51, wherein the external defibrillator stores a protocol that defines a progression of defibrillation shock energy levels and a number of defibrillation shocks for at least some of the energy levels, and the instructions that cause a programmable processor to estimate a number of defibrillation shocks comprise instructions that cause a programmable processor to estimate a number of defibrillation shocks according to the protocol that are available from the defibrillator based on the estimated amount of stored energy.

54. The computer-readable medium of claim 50, further comprising instructions that cause a programmable processor to estimate a total capacity of a plurality of energy storage devices of the medical device, wherein the instructions that cause a programmable processor to estimate a number of therapy delivery events comprise instructions that cause a programmable processor to estimate the number of therapy delivery events based on the estimated total amount of stored energy.

55. The computer-readable medium of claim 50, further comprising instructions that cause a programmable processor to:
estimate an amount of energy stored by each of a plurality energy storage devices of the medical device;
for each of the energy storage devices, estimate a number of therapy delivery events available from the medical device when the medical device is powered by the energy storage device based on the estimated amount of energy stored by the energy storage device; and
present the estimated number of therapy delivery events for each of the energy storage devices to the user.

56. A method comprising:
estimating an amount of energy stored by an energy storage device of a medical device that monitors a patient;

estimating, by the medical device, a remaining operational time for the medical device in each of a plurality of monitoring modes based on the estimated amount of stored energy; and presenting the estimated remaining operational times to a user, wherein presenting the remaining operational times to a user comprises displaying the remaining operational times via a display of the medical device.

57. The method of claim 56,
wherein estimating an amount of energy stored and a remaining operational time in each of a plurality of monitoring modes comprises periodically estimating the amount of energy stored and the remaining operational time in each of the plurality of monitoring modes, and displaying the estimated remaining operational times comprises:
displaying the estimated remaining operational times substantially continuously via the display of the medical device when the medical device is operational; and
periodically updating the displayed remaining operational times.

58. The method of claim 56,
wherein estimating an amount of energy stored by an energy storage device of the medical device comprises estimating a total amount of energy stored by a plurality of energy storage devices of the medical device, and
estimating a remaining operational time for the medical device comprises estimating the remaining operational time for the medical device in each of the monitoring modes based on the estimated total amount of stored energy.

59. The method of claim 56,
wherein estimating an amount of energy stored by an energy storage device of the medical device comprises estimating an amount of energy stored by each of a plurality of energy storage devices of the medical device, and
wherein estimating a remaining operational time for the medical device comprises, for each of the energy storage devices, estimating the remaining operational time for the medical device in each of the monitoring modes when the medical device is powered by the energy storage device based on the estimated capacity of the energy storage device.

60. The method of claim 56, wherein the medical device comprises an external defibrillator.

61. The method of claim 56, wherein estimating an amount of energy stored by an energy storage device comprises estimating an amount of energy stored by a battery.

62. The method of claim 56, wherein the medical device also delivers therapy to the patient, further comprising:
storing a value that indicates an estimated number of therapy delivery events available from the medical device;
periodically estimating the amount of amount of energy stored by the energy storage device of the medical device;
periodically estimating a number of therapy delivery events available from the medical device based on the estimated amounts of stored energy to produce updated estimates;
periodically updating the value based on the updated estimates; and
presenting the value to the user.

63. A device comprising:
a user interface; and
a processor configured to estimate an amount of energy stored by an energy storage device of a medical device that monitors a patient, estimate a remaining operational time for the medical device in each of a plurality of monitoring modes based on the estimated amount of stored energy, and present the estimated remaining operational times to a user.

64. The device of claim 63, wherein the medical device also delivers therapy to the patient, wherein the processor stores a value that indicates an estimated number of therapy delivery events available from the medical device, periodically estimates the amount of amount of energy stored by the energy storage device of the medical device, periodically estimates a number of therapy delivery events available from the medical device based on the estimated amounts of stored energy to produce updated estimates, periodically updates the value based on the updated estimates and presents the value to the user.

65. The device of claim 63, wherein the processor estimates a first remaining operational time for the medical device in a first monitoring mode that includes at least one of electrocardiogram monitoring, oxygen saturation monitoring, or temperature monitoring, and estimates a second remaining operational time for the medical device in a second monitoring mode that includes at least one of non-invasive blood pressure monitoring or partial pressure of carbon dioxide monitoring.

66. The device of claim 63, further comprising a display, wherein the processor displays the estimated remaining operational times to the user via the display.

67. The device of claim 66, wherein the processor periodically estimates the amount of energy stored by the energy storage device and the remaining operational time in each of the plurality of monitoring modes, displays the estimated remaining operational times substantially continuously via the display when the device is operational, and periodically updates the displayed remaining operational times.

68. The device of claim 63, wherein the processor estimates a total capacity of a plurality of energy storage devices of the medical device, and estimates the remaining operational time for the medical device in each of the monitoring modes based on the estimated total amount of stored energy.

69. The device of claim 63, wherein the processor estimates an amount of energy stored by each of a plurality of energy storage devices of the medical device, and, for each of the energy storage devices, estimates the remaining operational time for the medical device in each of the monitoring modes when the medical device is powered by the energy storage device based on the estimated amount of energy stored by the energy storage device.

70. The device of claim 63, wherein the device comprises the medical device.

71. The device of claim 70, wherein the medical device comprises an external defibrillator.

72. The device of claim 63, wherein the device comprises the energy storage device.

73. The device of claim 63, wherein the energy storage device comprises a battery.

74. A non-transitory computer-readable medium comprising instructions that cause a programmable processor to:
estimate an amount of energy stored by an energy storage device of a medical device that monitors a patient;

estimate a remaining operational time for the medical device in each of a plurality of monitoring modes based on the estimated amount of stored energy; and present the estimated remaining operational times to a user.

75. The computer-readable medium of claim 74, wherein the medical device also delivers therapy to the patient, wherein the computer-readable medium comprises further instructions that cause the programmable processor to:

store a value that indicates an estimated number of therapy delivery events available from the medical device;

periodically estimate a number of therapy delivery events available from the medical device based on the estimated amounts of stored energy to produce updated estimates;

periodically update the value based on the updated estimates; and present the value to the user.

* * * * *

UNITED STATES PATENT AND TRADEMARK OFFICE
CERTIFICATE OF CORRECTION

| | | |
|---|---|---|
| PATENT NO. | : 7,813,800 B2 | Page 1 of 1 |
| APPLICATION NO. | : 10/964509 | |
| DATED | : October 12, 2010 | |
| INVENTOR(S) | : Fleenor et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this
Fourth Day of October, 2011

David J. Kappos
*Director of the United States Patent and Trademark Office*